(12) United States Patent
Kusleika

(10) Patent No.: US 8,562,637 B2
(45) Date of Patent: *Oct. 22, 2013

(54) TEMPORARY VASCULAR FILTER

(75) Inventor: Richard S. Kusleika, Eden Prairie, MN (US)

(73) Assignee: Covidien LP, Mansfield, MA (US)

( * ) Notice: Subject to any disclaimer, the term of this patent is extended or adjusted under 35 U.S.C. 154(b) by 3266 days.

This patent is subject to a terminal disclaimer.

(21) Appl. No.: 10/682,696

(22) Filed: Oct. 9, 2003

(65) Prior Publication Data

US 2004/0102807 A1     May 27, 2004

Related U.S. Application Data

(63) Continuation of application No. 09/824,910, filed on Apr. 3, 2001, now abandoned, which is a continuation of application No. 09/400,159, filed on Sep. 21, 1999, now Pat. No. 6,325,815.

(51) Int. Cl.
*A61M 29/00*     (2006.01)
(52) U.S. Cl.
USPC .......................................................... 606/200
(58) Field of Classification Search
USPC .......................................................... 606/200
See application file for complete search history.

(56) References Cited

U.S. PATENT DOCUMENTS

| | | | |
|---|---|---|---|
| 4,425,908 A | 1/1984 | Simon | |
| 4,619,246 A | 10/1986 | Molgaard-Nielsen et al. | |
| 4,665,906 A | 5/1987 | Jervis | |
| 4,723,549 A | 2/1988 | Wholey et al. | |
| 4,873,978 A | 10/1989 | Ginsburg | |
| 4,926,858 A | 5/1990 | Gifford, III et al. | |
| 5,041,093 A | 8/1991 | Chu | |

(Continued)

FOREIGN PATENT DOCUMENTS

| | | |
|---|---|---|
| DE | 197 23 700 A1 | 12/1998 |
| EP | 0 820 729 A1 | 1/1998 |

(Continued)

OTHER PUBLICATIONS

Jul. 30, 2009 European Search Report and Written Opinion for European Application No. EP 07 07 5439 (7 pages).

*Primary Examiner* — Melanie Tyson
(74) *Attorney, Agent, or Firm* — Alana T. Bergman, Esq.

(57) ABSTRACT

The present invention provides a method of deploying a medical filter within a channel in a patient's body and filter systems which can be used in such a method. Such a filter may include a radially expandable body 52 having an opening 56 in a proximal length thereof. In one method, the filter is urged along a length of the channel with the filter body in a radially reduced configuration. This body is expanded to substantially fill the lumen of the vessel and orient the opening in the body proximally. Body fluid is permitted to enter the filter body through the proximally oriented opening and pass distally through the distal length of the body so that the distal length of the body filters from the body fluid particulate material entrained therein. The proximal length of the body can be drawn into the retrieval catheter, thereby effectively closing the proximally oriented opening within the catheter to retain the particulate material within the enclosure. In a preferred embodiment, the filter body 52 is formed of a porous, resilient fabric having pores therein and the proximal opening 56 is at least five times the size of such pores.

24 Claims, 4 Drawing Sheets

(56) References Cited

U.S. PATENT DOCUMENTS

| | | | | |
|---|---|---|---|---|
| 5,067,957 | A | 11/1991 | Jervis | |
| 5,071,407 | A | 12/1991 | Termin et al. | |
| 5,108,419 | A | 4/1992 | Reger et al. | |
| 5,152,777 | A | 10/1992 | Goldberg et al. | |
| 5,160,342 | A | 11/1992 | Reger et al. | |
| 5,171,233 | A | 12/1992 | Amplatz et al. | |
| 5,190,546 | A | 3/1993 | Jervis | |
| 5,192,286 | A | 3/1993 | Phan et al. | |
| 5,221,261 | A | 6/1993 | Termin et al. | |
| 5,224,945 | A * | 7/1993 | Pannek, Jr. | 606/159 |
| 5,341,818 | A | 8/1994 | Abrams et al. | |
| 5,496,277 | A | 3/1996 | Termin et al. | |
| 5,556,389 | A | 9/1996 | Liprie | |
| 5,597,378 | A | 1/1997 | Jervis | |
| 5,681,347 | A | 10/1997 | Cathcart et al. | |
| 5,695,519 | A | 12/1997 | Summers et al. | |
| 5,725,550 | A | 3/1998 | Nadal | |
| 5,814,064 | A | 9/1998 | Daniel et al. | |
| 5,827,324 | A | 10/1998 | Cassell et al. | |
| 5,910,154 | A | 6/1999 | Tsugita et al. | |
| 5,911,734 | A | 6/1999 | Tsugita et al. | |
| 5,941,869 | A * | 8/1999 | Patterson et al. | 604/508 |
| 6,001,118 | A | 12/1999 | Daniel et al. | |
| 6,027,520 | A | 2/2000 | Tsugita et al. | |
| 6,050,972 | A | 4/2000 | Zadno-Azizi et al. | |
| 6,059,814 | A * | 5/2000 | Ladd | 606/200 |
| 6,096,053 | A | 8/2000 | Bates | |
| 6,123,715 | A | 9/2000 | Amplatz | |
| 6,129,739 | A | 10/2000 | Khosravi | |
| 6,142,987 | A | 11/2000 | Tsugita | |
| 6,152,946 | A | 11/2000 | Broome et al. | |
| 6,171,327 | B1 | 1/2001 | Daniel et al. | |
| 6,179,859 | B1 | 1/2001 | Bates et al. | |
| 6,179,861 | B1 | 1/2001 | Khosravi et al. | |
| 6,214,026 | B1 | 4/2001 | Lepak et al. | |
| 6,231,588 | B1 | 5/2001 | Zadno-Azizi | |
| 6,245,012 | B1 | 6/2001 | Kleshinski | |
| 6,245,089 | B1 | 6/2001 | Daniel et al. | |
| 6,270,477 | B1 | 8/2001 | Bagaoisan et al. | |
| 6,287,321 | B1 | 9/2001 | Jang | |
| 6,325,815 | B1 * | 12/2001 | Kusleika et al. | 606/200 |
| 6,336,934 | B1 * | 1/2002 | Gilson et al. | 606/200 |
| 6,346,116 | B1 | 2/2002 | Brooks et al. | |
| 6,371,971 | B1 | 4/2002 | Tsugita et al. | |
| 6,537,295 | B2 | 3/2003 | Peterson | |
| 6,544,276 | B1 | 4/2003 | Azizi | |
| 6,589,263 | B1 | 7/2003 | Hopkins et al. | |
| 6,602,271 | B2 | 8/2003 | Adams et al. | |
| 6,605,102 | B1 | 8/2003 | Mazzocchi et al. | |
| 6,616,680 | B1 | 9/2003 | Thielen | |
| 6,663,652 | B2 | 12/2003 | Daniel et al. | |
| 6,676,682 | B1 | 1/2004 | Tsugita et al. | |
| 6,761,727 | B1 | 7/2004 | Ladd | |
| 6,843,798 | B2 * | 1/2005 | Kusleika et al. | 606/200 |
| 6,872,216 | B2 | 3/2005 | Daniel et al. | |
| 6,986,778 | B2 | 1/2006 | Zadno-Azizi | |
| 7,094,249 | B1 | 8/2006 | Broome et al. | |
| 2001/0012951 | A1 | 8/2001 | Bates et al. | |
| 2001/0041908 | A1 | 11/2001 | Levinson et al. | |
| 2001/0044632 | A1 | 11/2001 | Daniel | |
| 2002/0082639 | A1 | 6/2002 | Broome et al. | |
| 2002/0123765 | A1 | 9/2002 | Sepetka et al. | |

FOREIGN PATENT DOCUMENTS

| | | |
|---|---|---|
| EP | 1 127 556 A2 | 8/2001 |
| EP | 1 181 900 A2 | 2/2002 |
| EP | 1 316 292 A1 | 6/2003 |
| EP | 1 351 737 B1 | 10/2003 |
| GB | 2020557 A | 11/1979 |
| WO | WO 94/24946 | 11/1994 |
| WO | WO 96/01591 | 1/1996 |
| WO | WO 98/39053 | 9/1998 |
| WO | WO 98/55045 | 12/1998 |
| WO | WO 99/23976 | 5/1999 |
| WO | WO 99/51167 | 10/1999 |
| WO | WO 00/07657 | 2/2000 |
| WO | WO 00/67669 | 11/2000 |
| WO | WO 00/67671 | 11/2000 |
| WO | WO 01/05329 A1 | 1/2001 |
| WO | WO 01/15629 | 3/2001 |
| WO | WO 01/21100 | 3/2001 |
| WO | WO 01/35857 A1 | 5/2001 |
| WO | WO 01/50982 A1 | 7/2001 |
| WO | WO 01/52768 | 7/2001 |
| WO | WO 01/80777 | 11/2001 |

* cited by examiner

TEMPORARY VASCULAR FILTER

This application is a continuation of U.S. Ser. No. 09/824,910, filed Apr. 3, 2001 now abandoned, which is a continuation of U.S. Ser. No. 09/400,159, filed Sep. 21, 1999, now U.S. Pat. No. 6,325,815 B1, issued Dec. 4, 2001, the contents of each of which are hereby incorporated by reference in this application.

FIELD OF THE INVENTION

The present invention generally relates to filters for body passageways, and has particular utility in connection with temporary vascular filters.

BACKGROUND OF THE INVENTION

Filters can be deployed in channels or vessels in patient's bodies in a variety of medical procedures or in treating certain conditions. For example, rotating burrs are used in removing atheroma from the lumen of patients' blood vessels. These burrs can effectively dislodge the atheroma, but the dislodged material will simply float downstream with the flow of blood through the vessel. Filters can be used to capture such dislodged material before it is allowed to drift too far downstream, possibly occluding blood flow through a more narrow vessel.

Some researchers have proposed various traps or filters for capturing the particulate matter released or created in such procedures. However, most such filters generally have not proven to be exceptionally effective in actual use. These filters tend to be cumbersome to use and accurate deployment is problematic because if they are not properly seated in the vessel they can drift to a more distal site where they are likely to do more harm than good. In addition, these filters are generally capable of only trapping relatively large thrombi and are not effective for removing smaller embolic particles from the blood stream.

The problems with most temporary filters, which are intended to be used only during a particular procedure then retracted with the thrombi trapped therein, are more pronounced. Even if the trap does effectively capture the dislodged material, it has proven to be relatively difficult or complex to retract the trap back into the catheter through which it was delivered without simply dumping the trapped thrombi back into the blood stream, defeating the purpose of the temporary filter device. For this reason, most atherectomy devices and the like tend to aspirate the patient's blood during the procedure to remove the dislodged material entrained therein.

One promising filter design which overcomes many of these difficulties is shown in International Publication No. WO 96/01591 (the publication of PCT International Application No. PCT/US95/08613), the teachings of which are incorporated herein by reference. Generally, this reference teaches a trap which can be used to filter particles from blood or other fluid moving through a body vessel. In one illustrated embodiment, this trap includes a basket 270 which can be deployed and retracted through a catheter or the like, making it particularly suitable for use in minimally invasive procedures such as angioplasty or atherectomy procedures. The fact that this trap is optimally carried on a mandrel 260 further enhances its utility as most common angioplasty balloons and atherectomy devices are used in conjunction with such mandrels. While this trap is very useful and shows great promise in many common procedures, it may be possible to better retain the thrombi collected in the filter during retrieval of the filter.

SUMMARY OF THE INVENTION

The present invention provides a method of deploying a medical filter within a channel in a patient's body and devices which are well suited for use in such procedures. In accordance with one method of the invention, a filter and retrieval catheter are provided. This filter has a radially expandable body having proximal and distal ends and which defines an enclosure. The expandable body has a distal length and a proximal length which includes an opening therein. The retrieval catheter has a lumen with a diameter less than the maximum dimension of the body's expanded configuration. This filter is urged along a length of the channel in the patient's body with the filter body in a radially reduced configuration. The body is radially expanded to its expanded configuration such that it substantially fills the lumen of the vessel and the opening in the body is oriented proximally. Body fluid is permitted to enter the enclosure through this proximally oriented opening and is permitted to pass through the distal length of the body. In so doing, the distal length of the body filters from the body fluid particulate material entrained therein (assuming, of course, that there is any such particulate material of an appropriate size). The proximal length of the body is drawn within the lumen of the catheter, thereby effectively closing the proximally oriented opening within the retrieval sheath to retain said particulate material within the enclosure.

Further refinements of this method are envisioned. For example, in one embodiment, the filter has a narrow proximal end which is smaller than the lumen of the catheter. In drawing the proximal length of the filter within the catheter, this narrow proximal end may be introduced into the distal end of the catheter's lumen. The filter may then be retracted until the internal surface of the catheter engages the body of the filter distally of the opening to effectively create a particulate seal therebetween.

As noted above, the present invention also encompasses a device well suited for use in such procedures. In one embodiment, such a device comprises a collapsible filter system including a mandrel and a filter. The mandrel has proximal and distal ends and the filter is carried along the mandrel between these ends. The filter has a radially expandable body having proximal and distal ends of its own. The body is formed of a porous, resilient fabric having pores therein through which a body fluid may pass, but which are small enough to restrict passage of particulate material over a certain, predetermined size entrained in the body fluid. A proximally oriented hole passes through the fabric along a proximal length of the filter's body. This hole is spaced distally of the proximal end of the body and being at least about five times the size of said pores.

DETAILED DESCRIPTION OF THE PREFERRED EMBODIMENTS

Figure 1:
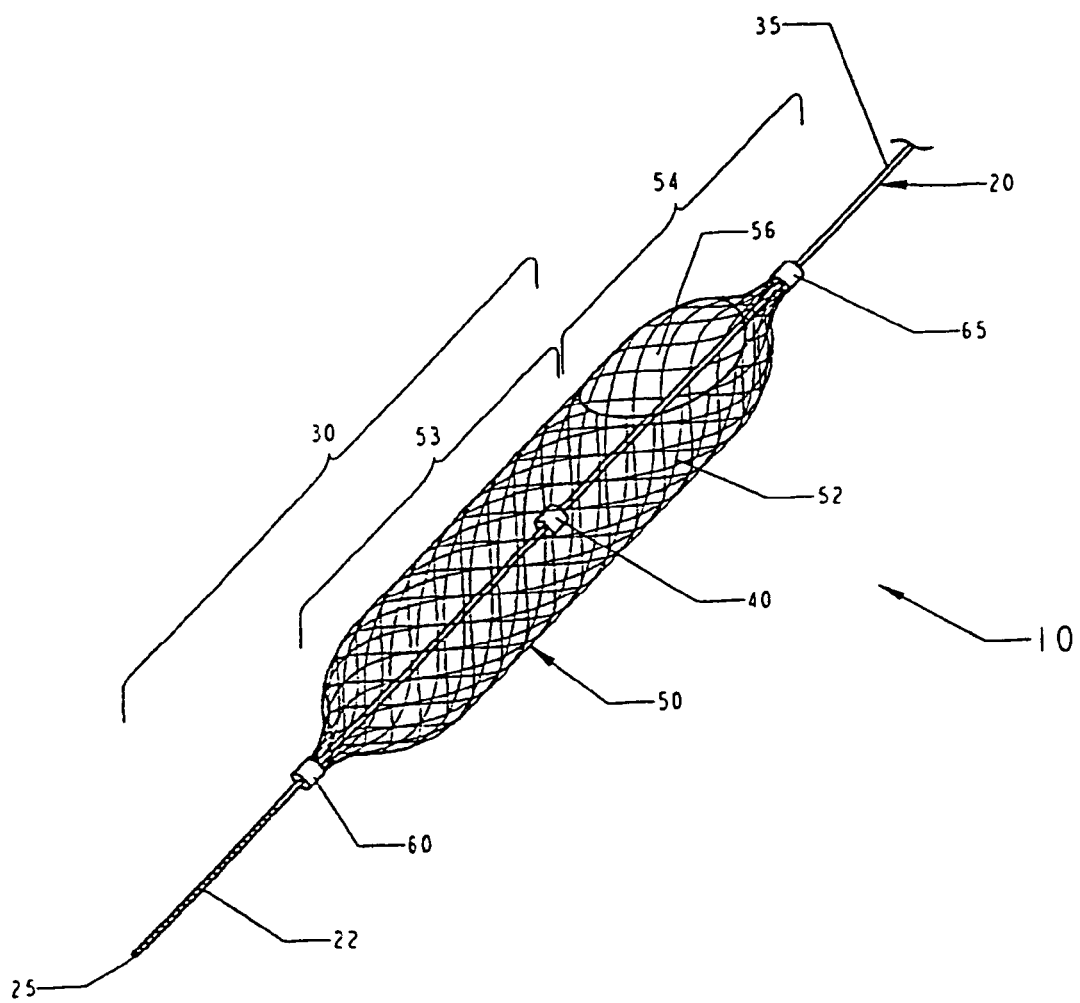
FIG. 1 is a perspective view of a medical filter in accordance with one embodiment of the present invention.
Figure 2:
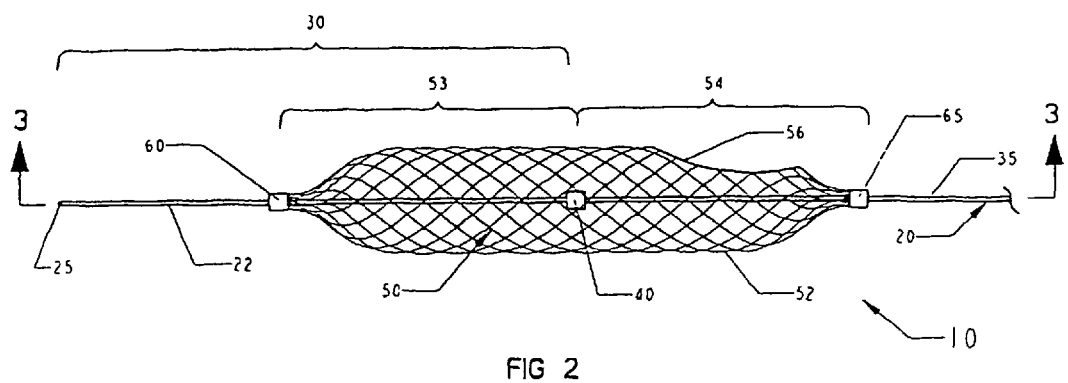
FIG. 2 is a side elevation view of the filter of FIG. 1.
Figure 3:
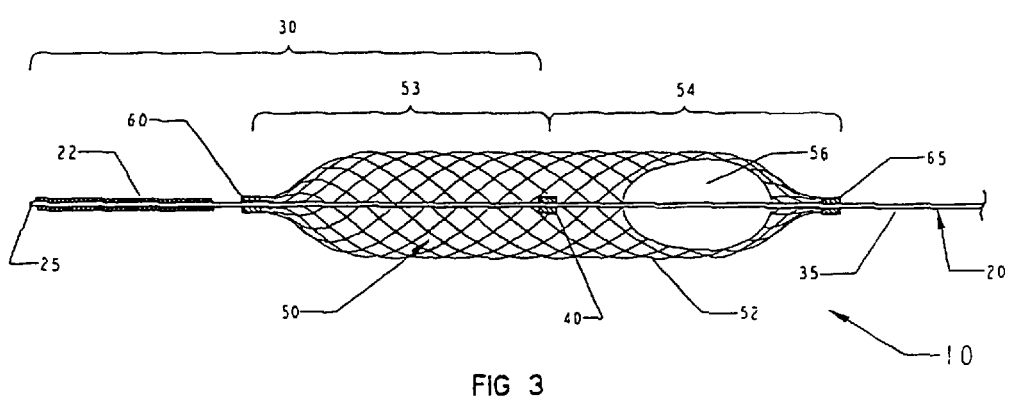
FIG. 3 is a cross sectional view of the medical filter of claim 1, taken along line 3-3 of FIG. 2.

FIGS. 1-3 illustrate a filter system 10 in accordance with one embodiment of the invention. This filter system can be used in any channel in a patient's body, including blood vessels, the urinary tract or biliary tract and airways. This filter system 10 is optimally designed to be deployed in a patient's vessel in a minimally invasive procedure, such as by introducing the filter system into a blood vessel through a catheter (as described in greater detail below).

The filter system 10 of the invention generally includes a mandrel 20 and a filter 50. Conceptually, the mandrel 20 can be thought of as having a primary function of positioning and controlling the deployment of the filter 50 while the filter can be considered the primary therapeutic or functional element of the system 10.

The mandrel 20 should be fairly flexible to allow the device to be deployed in a curving body passageway without kinking or otherwise inhibiting suitable deployment of the filter 50. While the mandrel can be formed of any material having any dimension suitable for the task for which the filter system 10 is to be employed, in most circumstances, the mandrel 20 will comprise an elongate metal wire. In one particularly preferred embodiment, the mandrel 20 is formed of nitinol, a roughly stoichiometric alloy of nickel and titanium having excellent "superelastic" properties. The use of nitinol in medical guidewires and related applications is well known in the art and need not be discussed in detail here. If so desired, the distal-most length of the mandrel may include a flexible helically wound coil 22 extending thereover. The use of such helical coils to enhance flexibility of the distal tip is well known in the guidewire art.

The mandrel 20 shown in FIGS. 1-3 has an enlarged diameter stop 40 attached thereto. The stop 40 is spaced proximally from the distal tip 25 of the mandrel 20. Desirably, the stop 40 is spaced proximally of the proximal end of the helical coil 22 of the mandrel. This permits the distal slider 60 of the filter 50 to slide relatively freely and unencumbered along the length of the mandrel distally of the stop.

The stop 40 can be formed of any desired material and can be attached to the mandrel 20 in any desired fashion. The stop should be attached to the mandrel relatively securely, though, as the stop will be used to urge the filter 50 within the lumen of the vessel in which the system 10 is to be deployed. As an example, the stop 40 may comprise a standard radiopaque marker band which has been securely crimped on the mandrel 20 and/or attached to the mandrel using an adhesive or solder. The precise length and shape of the stop 40 is not critical. The drawings illustrate the stop 40 as a relatively short cylindrical body attached about the circumference of the mandrel. However, the stop 40 may have a more bulbous shape and could, in theory, even be formed integrally with the mandrel.

The stop 40 effectively divides the mandrel into distal and proximal lengths. The distal length 30 of the mandrel can be thought of as that length which extends distally from the stop 40 to the distal tip 25 of the mandrel. Likewise, the proximal portion 35 of the mandrel 20 can be thought of as comprising the length of the mandrel extending proximally from the stop 40 to the proximal end of the mandrel.

The filter 50 shown in FIGS. 1-3 has an elongate, generally tubular body 52 which extends from a distal slider 60 proximally to a proximal slider 65. The body 52 of the filter can be formed of any material suitable for the application at hand. In many applications, e.g., filtering blood within a patient's vasculature, the filter body 52 typically comprises a length of a braided tubular fabric. The use of a tubular braid of nitinol to make medical devices is described in some detail in International Publication No. WO 96/01591, the teachings of which were incorporated above by reference. Briefly speaking though, this process can employ a tubular braid of a fabric comprising two sets of nitinol wires wrapped helically about a mandrel, with one set of wires being wrapped spirally about the mandrel in one direction and the other set being wrapped in the other direction. This braid is then placed in contact with a molding surface of a molding element which defines the shape of the desired functional element. By heat treating the fabric in contact with the molding surface of the molding element, one can create a functional element having virtually any desired shape.

The body 52 of the filter 50 desirably is made of a fairly flexible, resilient material. In particular, the filter 52 desirably has a radially expanded configuration, e.g., the shape shown in FIGS. 1-3, which the device will tend to resiliently assume in the absence of any countervailing biasing force. A body 52 formed of a nitinol tubular braid which has been heat set into the desired shape should suit this purpose well.

In the filter system 10 shown in FIGS. 1-3, the body 52 of the filter 50 assumes a generally tubular shape having tapered proximal and distal ends. The maximum outer diameter of the middle length of the body 52 should be sized to substantially fill the lumen of a vessel to ensure that the filter will effectively preclude any emboli (or other particulate material which may be entrained in the patient's bloodstream) from passing around the filter.

The body of the filter includes a distal length 53 and a proximal length 54, each of which tapers from the middle of the body's length to their respective ends. In particular, the distal length 53 tapers distally toward a narrow distal end adjacent the distal slider 60 while the proximal length 54 of the filter body tapers toward its proximal end adjacent the proximal slider 65. The rate of this tapering can be varied as desired. While FIGS. 1-3 illustrate a fairly gradual taper, the change in diameter may be more abrupt. The filter body 52 of FIGS. 1-3 is also fairly symmetrical, with the tapers of the proximal and distal lengths being about the same. In some circumstances it may be advantageous to have the two lengths taper differently, e.g. where the proximal length tapers more gradually while the distal length changes diameter more abruptly.

The proximal length 54 of the filter body has at least one proximally oriented opening 56 therein. This opening passes through the flexible, resilient fabric of which the body 52 desirably is formed. The fabric has pores therein which allow fluids to pass therethrough, but the pores are small enough to prevent passage of particles larger than a predetermined size. If the body is formed of a metallic tubular braid as mentioned above, the maximum sizes of these pores can be controlled by adjusting the number of wires in the braid and the pick and pitch of the braid. For example, if the filter 50 is to be employed as a vascular filter, a pore size of 20-1500 microns is desirable. If such a filter body has a maximum diameter of about 4 mm, it may be formed of 48 wires each having a diameter of about 0.002 inches (about 50 microns) and a pick rate of about 90 per inch (about 35 per centimer).

The size of the proximally oriented opening 56 should be sufficient to permit body fluid with particulate material entrained therein to enter the enclosure within the body 52 of the filter. At a minimum, it is expected that the opening will be at leas five times the maximum pore size of the fabric of which the body is formed, with an opening of at least ten times the maximum pore size being preferred.

The opening 56 can be formed in any suitable fashion. If the filter is formed from a preformed flat sheet of fabric wrapped into the desired shape, the opening can be cut through the fabric before the fabric is shaped into the filter body. If the body 52 is formed of a tubular metallic braid, it may instead be cut through the fabric after the braid is heat set in the desired shape.

In one particularly preferred method of forming the filter (which method comprises another embodiment of the invention), a tubular metal braid is provided. The distal and proximal sliders 60, 65 are attached to the braid a suitable distance from one another. The braid is trimmed at the distal end of the distal slider 60 and at the proximal end of the proximal slider 65. A forming mandrel (not shown) is passed between the wire strands of the braid and positioned within the tubular braid.

The forming mandrel has an external molding surface which generally coincides with the desired shape of the filter body. The forming mandrel may have a larger diameter than the inner diameter of the tubular braid and the braid may be drawn down against the forming mandrel by applying axial tension to the braid. This structure may be heated at an elevated temperature to heat-set the filter body 52 in this shape and the forming mandrel may be removed.

The forming mandrel includes a proximal projection having a periphery the size and shape of the desired proximal opening 56. This projection extends through the wire mesh of the tubular braid during heat treatment, forcing the wire strands to extend about the periphery of the projection. As a consequence of the heat treatment, when the forming mandrel is removed, the wires will retain the proximal opening without requiring cutting the fabric.

In FIGS. 1-3, the filter 50 is shown as having a single opening 56 extending over only one side of the proximal length 54 of the filter body (i.e., above the mandrel 20 in FIG. 2). To increase the percentage of body fluid which passes into the enclosure of the filter body, the number of openings or the shape of the opening(s) can be adjusted to maximize the cross sectional area of the vessel covered by the openings. For example, a plurality of openings can be spaced equiangularly about the proximal length 54, such as three openings arranged about 120 degrees from one another.

The opening 56 in FIGS. 1-3 is generally elliptical with a major axis extending generally in a plane which contains the axis of the mandrel 20. If one were to increase coverage of the opening 56 by adjusting its shape, the strength of the filter and its connection to the proximal slider 65 should not be compromised. One way to accomplish this is to offset the filter 50 with respect to the mandrel 20. In FIGS. 1-3, the body 52 of the filter is generally symmetrical about a central longitudinal axis and this axis generally coincides with the axis of the mandrel. One could instead make the filter asymmetrical, with the axis of the mandrel 20 spaced radially outwardly from the central axis of the body 52. In such a design, the mandrel could extend adjacent to one side of the body and the opposite side of the body would extend farther from the mandrel. By positioning the opening 56 on the larger side of the body, the opening can be made larger and cover more of the cross sectional area of the vessel in which the filter is deployed.

While the opening 56 can extend up to or even into the proximal slider 65, in a preferred embodiment the opening 56 is spaced distally from the slider 65 and the proximal end of the body 52. This will enable a more secure connection between the slider 65 and the body. The distal end of the opening desirably terminates proximally of the location where the filter body has its maximum diameter. This will minimize the chance that body fluid could slip between the filter and the wall of the vessel in which the filter is deployed. This will also provide a more effective seal between the filter body 52 and the catheter in which it is retrieved. (Such retrieval is discussed below in connection with FIGS. 7 and 8.)

The filter 50 is attached to or carried by the mandrel 20 by means of a proximal slider 65 attached to the body 52 adjacent its proximal end and a distal slider 60 attached adjacent the distal end of the body 52. The distal slider 60 should be free to slide along at least a proximal portion of the distal length 30 of the mandrel while the proximal slider 65 should be free to slide along at least a distal portion of the proximal length 35 of the mandrel. In use, the stop 40 of the mandrel effectively defines a limit on the range of motion of these sliders 60, 65.

While each of the sliders 60, 65 should be slidable along its respective length of the mandrel, the sliders can take any desired shape. In the illustrated embodiments, each slider comprises a relatively thin ring which is carried about the mandrel. The thin ring can be attached to the body 52 in any desired fashion, such as by crimping or swaging the fabric of the body between two layers of the ring or soldering, welding or otherwise adhering the fabric to the ring.

The stop 40 of the mandrel is positioned within the body 52 of the filter and is not exerting any biasing force on either of the sliders 60, 65. In this configuration, the mandrel 20 can be moved proximally and distally with respect to the filter 50 without substantially affecting the shape or position of the filter. The limits of this range of free movement of the mandrel with respect to the filter are generally defined by the relationship between the stop 40 and the sliders 60, 65. In particular, the mandrel can be moved from a distal position wherein the stop 40 abuts but does not exert any force on the distal slider 60 and a proximal position wherein the stop 40 abuts, but does not exert any significant force on, the proximal slider 65. This allows the filter 50 (or any other functional element which is carried by the mandrel) to be fairly precisely positioned within a patient's vessel and retain that position even if the guidewire is moved slightly during use. This can be advantageous in circumstances where other devices are exchanged over the guidewire (e.g., during angioplasty and atherectomy procedures).

The inner diameter of the generally annular collars defining the sliders 60, 65 is desirably larger than the outer diameter of the mandrel, but should be smaller than the outer diameter of the stop 40. In this fashion, the stop serves as an effective limit on proximal movement of the distal slider 60 and distal movement of the proximal slider 65. Apart from this relationship with the slider 40 and the fact that both sliders are indirectly linked to one another by the body 52 of the filter, the proximal and distal sliders are slidable along the mandrel essentially independently of one another.

When the mandrel 20 is urged distally (to the left in FIGS. 2 and 3) against the distal slider 60, the stop will exert a distal biasing force against the distal end of the body 52 of the filter. In theory, if the filter were used in a frictionless environment, the filter would travel with the mandrel without any appreciable alteration in the shape of the body 52. In most clinical applications, though, this is not the case. Instead, there is typically some force restraining completely free movement of the filter within the channel of the patient's body. Typically (and as suggested in FIGS. 5 and 6, for example), the body 52 of the filter will resiliently expand into physical contact with the interior surface of the vessel within which it is deployed. This contact with the vessel wall will tend to hold the filter 50 in place as the stop of the mandrel slides proximally and distally between the two sliders 60, 65. When the mandrel is urged distally until it exerts a distal force against the distal slider 60, this force will tend to axially elongate the body 52.

Resilient tubular braids tend to assume a radially reduced profile upon axial elongation. (This property and some of its implications are discussed in International Publication No. WO 96/01591, mentioned previously.) As a consequence, when the mandrel 20 is urged distally to push distally against the distal slider 60, this distal force acts against the restorative force of the resilient braid, which would otherwise bias the braid into its expanded configuration (FIGS. 1-3). By overcoming this restorative force with a countervailing distal force, the body 52 will tend to both axially elongate and assume a radially reduced profile. This, in turn, reduces the force with which the body engages the wall of the vessel or catheter in which the filter is positioned and reduces friction between the filter 50 and the vessel or catheter. Hence, urging the mandrel distally to move the filter 50 distally will, at the same time, reduce friction between the filter and the vessel wall to further facilitate advancement of the filter along the vessel's lumen. This requires less force to push the filter distally, enabling the mandrel to be smaller and reducing the outer diameter of the collapsed device, making deployment in smaller vessels feasible. In addition, the reduced friction between the filter and the vessel wall limits damage to the intima of the vessel, permitting the filter to be deployed and moved with a minimum of trauma.

When the mandrel is retracted proximally, the stop 40 of the mandrel will abut against, and exert a proximal biasing force on, the proximal slider 65 of the filter 50. This proximal biasing force will act against the restorative force of the body 52 to axially elongate and radially reduce that body. This permits the device to be withdrawn proximally along the lumen of the vessel either for repositioning at a more proximal location or for withdrawal from the patient's body at the end of the procedure.

In the embodiment of FIGS. 1-3, the proximal and distal sliders 60, 65 are free to move relatively independently of one another, limited primarily by their indirect link to one another through the body 52 of the filter. For example, when the mandrel 20 is urged distally against the distal slider 60 (FIG. 4), the proximal slider will slide proximally along the proximal length 35 of the mandrel. Similarly, when the mandrel is withdrawn proximally to urge proximally against the proximal slider 65, the distal slider will be free to drift distally along the distal length 30 of the mandrel. Ideally, there should be a sufficient distance between the distal shoulder of the stop 40 and the proximal end of the helical coil 22 at the distal end of the mandrel.

FIGS. 4-8 schematically depict one method of the invention utilizing an alternative filter design. Most of the elements of the filter 50' in FIGS. 4-8 are essentially the same as like elements in FIGS. 1-3, so the same reference numbers have been used for most elements in both sets of drawings. The primary differences between the filter 50' of FIGS. 4-8 and the filter 50 described above is that the stop 40 has been omitted in FIGS. 4-8 and the proximal slider 65' has been secured to the mandrel 20 at a fixed location. The distal slider 60 remains free to slide along the mandrel.

The body 52' of the filter 50' is shaped a little differently from the filter body 52 of FIGS. 1-3. This difference is not crucial and does not yield significantly different properties. Instead, the differences in the fully deployed shapes of the two filters 50, 50' are intended to highlight that the shape can vary without compromising the filter's function.

Figure 4:
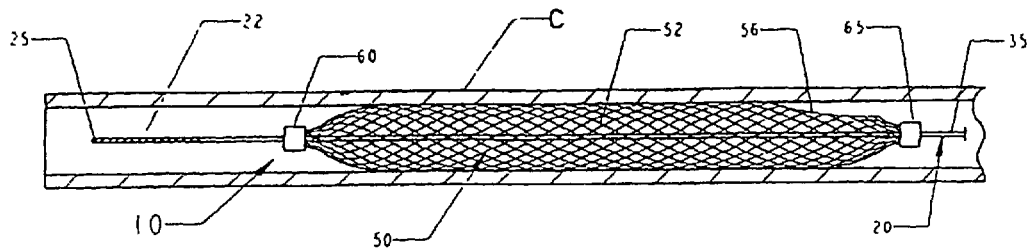
FIG. 4 is a schematic side view in partial cross section illustrating a filter of an alternative embodiment of the invention in a radially reduced configuration within a catheter.

FIG. 4 schematically illustrates the filter 50' collapsed within the lumen of a catheter C. The body 52' of the filter has been collapsed under the biasing force of the catheter walls into an axially elongated, radially reduced configuration. This catheter and filter combination may be advanced through a patient's body as a unit until a specific treatment site has been reached, but this combined unit may be difficult to steer through a more tortuous path. For many applications (e.g., deployment at a remote site within a patient's vasculature), the catheter will first be positioned adjacent the treatment site. Only then will the filter system be introduced into the distal end of the catheter C and urged along the catheter's lumen and the vessel V until the distal end 25 of the mandrel and the distal slider 65 are positioned adjacent the distal end of the catheter, as shown in FIG. 4.

Regardless of how the system reaches the state illustrated in FIG. 4, once the catheter is in place the filter 50' can be deployed out the distal end of the catheter. In particular, the filter 50' may be urged out of the distal end of the catheter, e.g., by holding the catheter C still and urging the mandrel 20 distally or by holding the mandrel 20 stationary and withdrawing the catheter C proximally.

Figure 5:
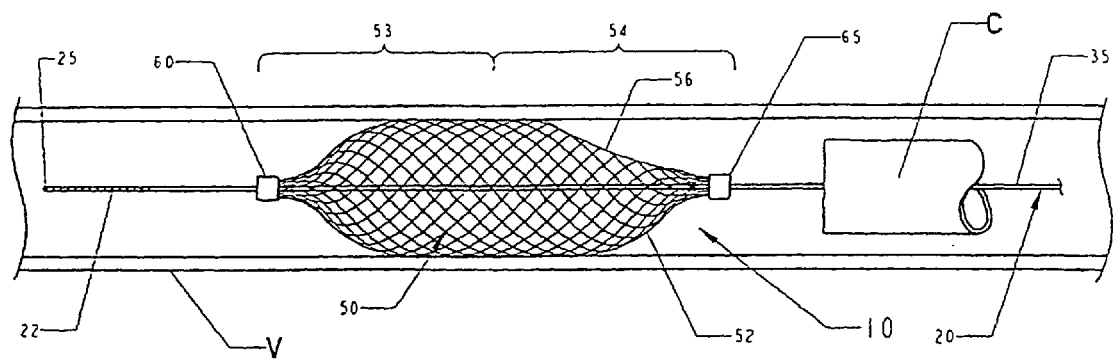
FIG. 5 is a schematic side view illustrating the filter of FIG. 4 deployed in a vessel in a patient's body.

Upon exiting the distal end of the catheter C, the flexible body 52 will resiliently expand radially outwardly, desirably until it engages the wall of the vessel V or, less desirably, is positioned adjacent to the vessel wall. (Such a configuration is shown in FIG. 5.) This will help ensure that all fluid passing along the vessel V will have to pass through the filter body 52'.

Figure 6:
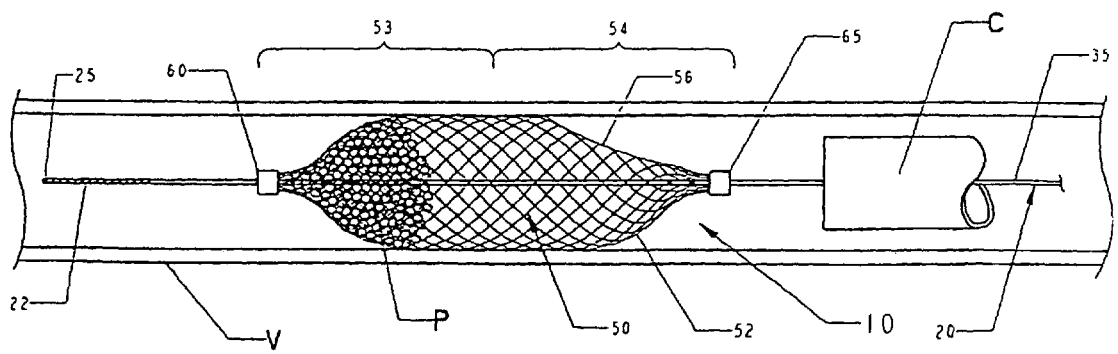
FIG. 6 is a schematic side view of the filter of FIGS. 4 and 5 with collected particulate material trapped within the filter.

A substantial portion (ideally, all or at least a vast majority) of the body fluid in the vessel should pass through the proximally oriented opening 56 in the filter body. Since the opening is fairly large, it is anticipated that any particulate material entrained in the body fluid travelling through the vessel will enter the interior of the filter through the opening 56. The pores in the distal length 53 of the filter body are significantly smaller, though, so most oversized particles will be trapped within the enclosure of the filter body. FIG. 6 schematically depicts such a situation, with a number of individual particles P being shown trapped within the filter body. If the filter 50 or 50' is to be used in a vascular procedure, the pores should be large enough to permit red blood cells to pass therethrough, but small enough to trap thrombi or emboli above a certain predetermined size.

A wide variety of vascular filters are known in the art and the ease with which such filters can be deployed varies. One of the primary distinguishing characteristics between these various filter designs is the ease with which the filters can be withdrawn from or repositioned within the patient's body. For example, most commercially available vena cava filters are provided with sharp barbs or other structures which firmly seat the devices in a wall of the vessel, but which effectively preclude retraction of the device. Temporary filters avoid such tenacious attachments to the vessel wall, permitting them to be retracted or moved after initial deployment. As noted above, though, one of the primary difficulties encountered in using such temporary filters is the risk of dumping the captured particulate material back into the vessel from which it was filtered. Many designs require that the physician first aspirate the particulate material or, in the case of thrombi captured in vascular procedures, use drugs which help break down the particles to clinically acceptable sizes.

International Publication No. WO 96/01591, mentioned previously, provides a particularly useful filter. This filter, which may be generally dome-shaped and have a proximally-facing lip, enables a physician to close the filter prior to retraction, keeping the captured particles within the filter during removal or repositioning. Unfortunately, this design is mechanically complex. In one embodiment disclosed therein, the filter is provided with a drawstring which can be used to draw the proximal edge of the filter down toward the wire on which it is carried, minimizing the risk of losing the particles. A second design proposed in this reference employs a separately deployable cover which can be brought into sealing engagement with the filter. While this may further reduce the risk of dumping particles back into the vessel, the increased mechanical complexity makes it difficult to provide a highly reliable, cost-effective device.

Figure 7:
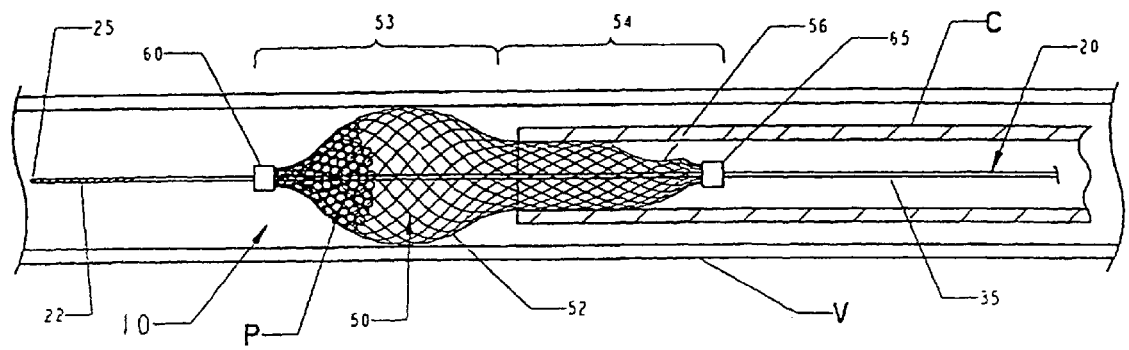
FIG. 7 is a schematic side view of the filter of FIGS. 4-6 drawn far enough into the catheter to effectively close the proximally oriented opening within the catheter.

The present invention provides an elegant solution to these difficulties which minimizes mechanical complexity and promises to provide very effective containment of filtered particles. FIG. 7 shows the filter 50' of FIGS. 4-6 partially retracted into the catheter C. If the filter is being used for only a short period of time, the catheter C may be the same catheter used to initially deploy the filter in the vessel. If the filter is to be left in place for a longer period of time, though, it may be preferred to remove the deployment catheter (FIG. 4) from the patient's body and later introduce a separate retrieval catheter by advancing the retrieval catheter along the mandrel 20.

The lumen of the retrieval catheter C in FIG. 7 has a diameter smaller than the maximum cross-sectional dimension of the body's expanded configuration. The lumen is larger than the narrow proximal end of the filter body 52' adjacent the proximal slider 65', though, and the illustrated filter body is spaced from the vessel wall about its entire periphery. As a consequence, the distal tip of the catheter can be positioned between the proximal end of the body 52' and the wall of the vessel V before the catheter engages the body of the filter adjacent the slider. This can be done by holding the catheter in place and withdrawing the mandrel proximally, by holding the mandrel stationary and moving the catheter distally, or moving both the catheter and the mandrel.

Once the proximal end of the body 52' is introduced into the catheters lumen, the rest of the body can be drawn into the lumen of the catheter. Again, the body can be drawn into the catheter by advancing the catheter distally or retracing the filter proximally. At some point, the wall of the catheter C will engage the larger diameter body 52. Ideally, the lumen of the catheter is notably smaller than the deployed diameter of the filter body. As shown in FIG. 7, in this case the walls of the catheter will exert a biasing force to urge the body toward the radially reduced configuration in which it was initially deployed (FIG. 4).

Perhaps more importantly, though, the internal surface of the catheter engages the body of the filter distally of the filter's proximally oriented opening 56. While the opening may still be open to the lumen of the catheter, the engagement between the filer body and the catheter wall distally of the opening effectively creates a particulate seal therebetween. As a consequence, simply by advancing the catheter C with respect to the filter 50', one can seal within the combined catheter and filter all of the captured particles above the predetermined minimum size. This combination can then be moved as a unit either to remove it from or reposition it within the patient's body with minimal risk of losing any of the captured particles.

Figure 8:
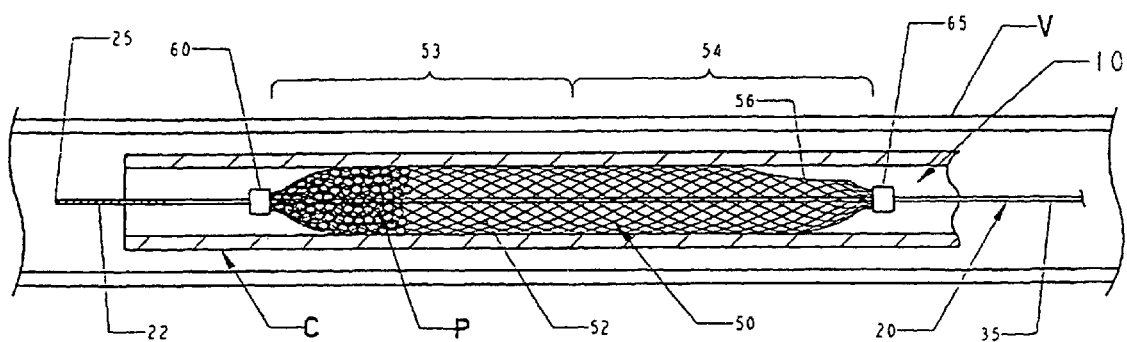
FIG. 8 is a schematic side view of the filter of FIGS. 4-7 withdrawn completely within the lumen of the catheter.

If the filter is to be completely withdrawn from the vessel, it is preferred that the filter body 52' be completely withdrawn into the lumen of the catheter (as shown in FIG. 8) rather than leaving a distal section of the filter extending out of the catheter (as shown in FIG. 7). This will reduce friction against the vessel wall, making withdrawal easier and reducing trauma to the intima of the vessel.

While a preferred embodiment of the present invention has been described, it should be understood that various changes, adaptations and modifications may be made therein without departing from the spirit of the invention and the scope of the appended claims.

What is claimed is:

1. An apparatus for filtering emboli from blood flowing through a vessel, the apparatus comprising:
   a guidewire having a distal region and a stop on the distal region; and
   a filter element configured to rotate and translate on the guidewire, the filter element having a proximal end and a distal end,
   wherein the stop is disposed intermediate the proximal and distal ends of the filter element.

2. An apparatus for filtering emboli from blood flowing through a vessel, the apparatus comprising:
   a guidewire having a distal region and a stop on the distal region; and
   a filter element having a proximal coupling slidably coupled to the guidewire proximal of the stop and a distal coupling slidably coupled to the guidewire distal of the stop;
   wherein the stop restricts translation of the filter element along the guidewire.

3. The apparatus of claim 2, wherein the filter element has a range of translation along the guidewire generally determined by the distance between the proximal coupling and the distal coupling.

4. The apparatus of claim 2, wherein translation of the filter element is restricted on the guidewire proximally by the distal coupling abutting against the stop, and distally by the proximal coupling abutting against the stop.

5. The apparatus of claim 2, wherein the filter element includes a filter sac coupled to the distal coupling.

6. An apparatus for filtering emboli from blood flowing through a vessel, the apparatus comprising:
   a guidewire having a diameter and a distal region;
   a filter element including a proximal ring slidably coupled to the guidewire and a distal ring slidably coupled to the guidewire, the proximal ring having a bore greater than the diameter of the guidewire and the distal ring having a bore greater than the diameter of the guidewire; and
   a stop disposed on the distal region of the guidewire intermediate the proximal ring and the distal ring.

7. The apparatus of claim 6, wherein stop has a diameter greater than the bore of the proximal ring.

8. The apparatus of claim 7, wherein the stop has a diameter greater than the bore of the distal ring.

9. The apparatus of claim 8, wherein translation of the filter element is restricted on the guidewire proximally by the distal ring abutting against the stop, and distally by the proximal ring abutting against the stop.

10. The apparatus of claim 6, wherein the filter element has a contracted state suitable for transluminal delivery, and the guidewire includes a distal region distal of the stop having a length greater than a length of the filter element in the contracted state.

11. An apparatus for filtering emboli from blood flowing through a vessel, the apparatus comprising:

a mandrel having a distal end and a stop spaced proximally of the distal end; and a vascular filter configured to rotate and translate on the mandrel, the vascular filter having a proximal end and a distal end, wherein the stop is disposed intermediate the proximal and distal ends of the vascular filter.

12. The apparatus of claim 11, further comprising a proximal slider disposed on the mandrel, and the vascular filter being connected to the proximal slider.

13. The apparatus of claim 12, further comprising a distal slider disposed on the guidewire, and the vascular filter being connected to the distal slider.

14. The apparatus of claim 13, wherein the stop is disposed intermediate of the proximal slider and the distal slider.

15. An apparatus for filtering emboli from blood flowing through a vessel, the apparatus comprising:

a mandrel having a distal end and a stop spaced proximally of the distal end; and a vascular filter having a proximal slider coupled to the mandrel proximal of the stop and a distal slider coupled to the mandrel distal of the stop;

wherein the stop restricts translation of the vascular filter along the mandrel.

16. The apparatus of claim 15, wherein the vascular filter has a range of translation along the mandrel generally determined by the distance between the proximal slider and the distal slider.

17. The apparatus of claim 15, wherein translation of the vascular filter is restricted on the mandrel proximally by the distal slider abutting against the stop, and distally by the proximal slider abutting against the stop.

18. The apparatus of claim 15, wherein the vascular filter is self-expanding.

19. An apparatus for filtering emboli from blood flowing through a vessel, the apparatus comprising:

a mandrel having a diameter and a distal region;

a vascular filter including a proximal slider coupled to the mandrel and a distal slider coupled to the mandrel, the proximal slider having a bore greater than the diameter of the mandrel and the distal slider having a bore greater than the diameter of the mandrel; and a stop disposed on the distal region of the mandrel intermediate the proximal slider and the distal slider.

20. The apparatus of claim 19, wherein the stop has a diameter greater than the bore of the proximal slider.

21. The apparatus of claim 20, wherein the stop has a diameter greater than the bore of the distal slider.

22. The apparatus of claim 21, wherein translation of the vascular filter is restricted on the mandrel proximally by the distal slider abutting against the stop, and distally by the proximal slider abutting against the stop.

23. The apparatus of claim 19, wherein the vascular filter is self-expanding.

24. The apparatus of claim 19, wherein the vascular filter has a contracted state suitable for transluminal delivery, and the mandrel includes a distal region distal of the stop having a length greater than a length of the vascular filter in the contracted state.

* * * * *